United States Patent
Weller et al.

(10) Patent No.: US 7,083,629 B2
(45) Date of Patent: Aug. 1, 2006

(54) OVERTUBE APPARATUS FOR INSERTION INTO A BODY

(75) Inventors: Gary Weller, Los Gatos, CA (US); Craig Gerbi, Mountain View, CA (US); James Gannoe, Redwood City, CA (US); Mark E. Deem, Mountain View, CA (US); Douglas S. Sutton, Pacifica, CA (US); Hanson S. Gifford, III, Woodside, CA (US); Bernard H. Andreas, Redwood City, CA (US); Ronald G. French, Santa Clara, CA (US)

(73) Assignee: Satiety, Inc., Palo Alto, CA (US)

( * ) Notice: Subject to any disclaimer, the term of this patent is extended or adjusted under 35 U.S.C. 154(b) by 341 days.

(21) Appl. No.: 10/155,362

(22) Filed: May 23, 2002

(65) Prior Publication Data
US 2003/0065359 A1    Apr. 3, 2003

Related U.S. Application Data

(63) Continuation-in-part of application No. 09/871,297, filed on May 30, 2001, now Pat. No. 6,558,400.

(51) Int. Cl.
*A61B 17/08* (2006.01)
(52) U.S. Cl. .................... 606/151; 606/153
(58) Field of Classification Search .............. 606/1, 606/108, 139, 142, 143, 151, 153, 157, 167, 606/213, 215, 216, 219; 227/19, 20, 25, 227/65, 175.1–182.1, 901, 902; 600/32, 600/101, 104, 106, 114, 131, 136–139, 153, 600/156, 201, 210, 217; 604/909
See application file for complete search history.

(56) References Cited

U.S. PATENT DOCUMENTS

| 4,402,445 A | 9/1983 | Green |
| 4,547,192 A | 10/1985 | Brodsky et al. |
| 4,610,383 A | 9/1986 | Rothfuss et al. |

(Continued)

FOREIGN PATENT DOCUMENTS

EP   0 174 843 B1   3/1986

(Continued)

OTHER PUBLICATIONS

U.S. Appl. No. 60/234,360, filed Sep. 22, 2000, Schurr.

*Primary Examiner*—Kim M. Lewis
(74) *Attorney, Agent, or Firm*—Fulwider Patton LLP

(57) ABSTRACT

An overtube apparatus for insertion into a body is described herein. The assembly includes an overtube having a lumen defined throughout. The distal end of the overtube member has two or more windows in apposition configured to draw in tissue via a vacuum. A drive tube, which also defines a lumen, is inserted and is freely adjustable within the overtube. A spiral or helical fastener, which is temporarily attached to the drive tube distal end, is positioned within the overtube lumen. Endoscopic devices can be inserted within the drive tube lumen and advanced past the distal ends of both the drive tube and overtube. A pump provides the vacuum to draw apposed regions of tissue from within a hollow body organ into the windows of the overtube. Once the tissue has been invaginated, the drive tube is rotated to advance the fastener into the tissue to fasten them together.

18 Claims, 13 Drawing Sheets

U.S. PATENT DOCUMENTS

| | | | |
|---|---|---|---|
| 4,790,294 A | 12/1988 | Allred, III et al. | |
| 4,841,888 A | 6/1989 | Mills et al. | |
| 5,037,021 A | 8/1991 | Mills et al. | |
| 5,156,609 A | 10/1992 | Nakao et al. | |
| 5,222,961 A | 6/1993 | Nakao et al. | |
| 5,327,914 A | 7/1994 | Shlain | |
| 5,330,486 A | 7/1994 | Wilk | |
| 5,330,503 A | 7/1994 | Yoon | |
| 5,345,949 A | 9/1994 | Shlain | |
| 5,355,897 A | 10/1994 | Pietrafitta et al. | |
| 5,382,231 A | 1/1995 | Shlain | |
| 5,403,326 A | 4/1995 | Harrison et al. | |
| 5,411,508 A | 5/1995 | Bessler et al. | |
| 5,437,291 A | 8/1995 | Pasricha et al. | |
| 5,549,621 A | 8/1996 | Bessler et al. | |
| 5,551,622 A | 9/1996 | Yoon | |
| 5,571,116 A | 11/1996 | Bolanos et al. | |
| 5,577,654 A * | 11/1996 | Bishop | 227/175.1 |
| 5,582,616 A | 12/1996 | Bolduc et al. | |
| 5,584,861 A | 12/1996 | Swain et al. | |
| 5,607,094 A | 3/1997 | Clark et al. | |
| 5,624,381 A | 4/1997 | Kieturakis | |
| 5,626,588 A | 5/1997 | Sauer et al. | |
| 5,651,769 A | 7/1997 | Waxman et al. | |
| 5,655,698 A | 8/1997 | Yoon | |
| 5,676,674 A | 10/1997 | Bolanos et al. | |
| 5,690,656 A | 11/1997 | Cope et al. | |
| 5,722,990 A | 3/1998 | Sugarbaker et al. | |
| 5,728,178 A | 3/1998 | Buffington et al. | |
| 5,749,893 A | 5/1998 | Vidal et al. | |
| 5,755,730 A | 5/1998 | Swain et al. | |
| 5,782,844 A | 7/1998 | Yoon et al. | |
| 5,792,153 A | 8/1998 | Swain et al. | |
| 5,810,851 A | 9/1998 | Yoon | |
| 5,810,882 A | 9/1998 | Bolduc et al. | |
| 5,824,008 A | 10/1998 | Bolduc et al. | |
| 5,827,298 A | 10/1998 | Hart et al. | |
| 5,868,141 A | 2/1999 | Ellias | |
| 5,887,594 A | 3/1999 | LoCicero, III | |
| 5,897,534 A | 4/1999 | Heim et al. | |
| 5,897,562 A | 4/1999 | Bolanos et al. | |
| 5,910,105 A | 6/1999 | Swain et al. | |
| 5,928,264 A | 7/1999 | Sugarbaker et al. | |
| 5,947,983 A | 9/1999 | Solar et al. | |
| 5,964,772 A | 10/1999 | Bolduc et al. | |
| 5,964,782 A | 10/1999 | Lafontaine et al. | |
| 5,972,001 A | 10/1999 | Yoon | |
| 5,976,161 A | 11/1999 | Kirsch et al. | |
| 6,042,538 A | 3/2000 | Puskas | |
| 6,067,991 A | 5/2000 | Forsell | |
| 6,113,609 A | 9/2000 | Adams | |
| 6,159,146 A | 12/2000 | El Gazayerli | |
| 6,165,183 A | 12/2000 | Kuehn et al. | |
| 6,179,195 B1 | 1/2001 | Adams et al. | |
| 6,197,022 B1 | 3/2001 | Baker | |
| 6,200,318 B1 | 3/2001 | Har-Shai et al. | |
| 6,231,561 B1 | 5/2001 | Frazier et al. | |
| 6,328,689 B1 | 12/2001 | Gonzalez et al. | |
| 6,447,533 B1 | 9/2002 | Adams | |
| 6,494,888 B1 | 12/2002 | Laufer et al. | |
| 6,506,196 B1 | 1/2003 | Laufer | |
| 6,558,400 B1 | 5/2003 | Deem et al. | |
| 6,773,441 B1 | 8/2004 | Laufer | |
| 6,835,200 B1 | 12/2004 | Laufer et al. | |
| 2002/0040226 A1 | 4/2002 | Laufer et al. | |
| 2002/0072761 A1* | 6/2002 | Abrams et al. | 606/190 |
| 2002/0078967 A1 | 6/2002 | Sixto, Jr. et al. | |
| 2002/0082621 A1 | 6/2002 | Schurr et al. | |
| 2002/0143346 A1 | 10/2002 | McGuckin, Jr. et al. | |
| 2002/0193816 A1 | 12/2002 | Laufer et al. | |
| 2003/0093117 A1 | 5/2003 | Saadat | |
| 2003/0109892 A1 | 6/2003 | Deem et al. | |
| 2003/0120265 A1 | 6/2003 | Deem et al. | |
| 2003/0120289 A1 | 6/2003 | McGuckin, Jr. et al. | |
| 2003/0158563 A1 | 8/2003 | McClellan et al. | |
| 2004/0024386 A1 | 2/2004 | Deem et al. | |
| 2004/0162568 A1 | 8/2004 | Saadat et al. | |
| 2004/0225183 A1 | 11/2004 | Michlitsch et al. | |

FOREIGN PATENT DOCUMENTS

| | | |
|---|---|---|
| WO | WO 99/53827 A1 | 10/1999 |
| WO | WO 00/78227 A1 | 12/2000 |
| WO | WO 00/78229 A1 | 12/2000 |
| WO | WO 02/24080 A2 | 3/2002 |
| WO | WO 03/007796 A2 | 1/2003 |
| WO | WO 03/105563 A2 | 12/2003 |
| WO | WO 03/105671 A2 | 12/2003 |

* cited by examiner

OVERTUBE APPARATUS FOR INSERTION INTO A BODY

CROSS-REFERENCE TO RELATED APPLICATIONS

This is a continuation-in-part of U.S. patent application Ser. No. 09/871,297 entitled "Obesity Treatment Tools and Methods" filed May 30, 2001, now U.S. Pat. No. 6,558,400, and incorporated herein by reference in its entirety.

TECHNICAL FIELD OF THE INVENTION

The present invention relates generally to apparatus and methods for facilitating the treatment of organ bodies. More particularly, the present invention relates to overtube devices and methods for their use.

BACKGROUND OF THE INVENTION

In surgically treating hollow body organs, e.g., the stomach, there are numerous conventional techniques and tools for effecting treatment. For instance, surgical procedures for obesity date back to 1889 (Billroth) with the earliest peer reviewed procedure being the jejuno-ileal bypass in 1954 (Kreman). A successful procedure is commonly defined as one that results in at least 50% excess weight loss at 2 years. Today, the most commonly done operation is the Roux-en-Y gastric bypass (RYGB), with around 35,000 performed annually in the U.S. Other forms of bariatric surgery include Fobi pouch, bilio-pancreatic diversion, and gastroplasty or "stomach stapling". The single existing procedure that involves an implanted device is the Lap-Band, which is a laparoscopically installed inflatable cuff that is placed around the top of the stomach just below the lower esophageal sphincter (LES). This device affects satiety only (no reduced caloric absorption).

The RYGB procedure is a procedure which has become very common in bariatric surgery. This procedure facilitates the movement of the jejunum to a high position by using a retrocolic Roux-en-Y limb. The procedure is generally performed through a 6–8 inch incision extending from the end of the breastbone to just above the navel. The stomach is completely divided into 2 unequal portions (a smaller upper and a larger lower gastric pouch) using an automatic stapling device with the raw surface reinforced with additional sutures. The upper pouch typically measures less than about 1 ounce or 20 cc, while the lower larger pouch remains generally intact and continues to secrete stomach juices flowing through the intestinal tract.

A segment of the small intestine (just distal of the duodenum or proximal of the jejunum) is then brought from the lower abdomen and joined with the upper pouch to form an end-to-end anastomosis created through a half-inch opening, also called the stoma. This segment of the small intestine is called the "Roux limb" and carries food from the upper pouch to the remainder of the intestines, where the food is digested. The remaining lower pouch and the attached segment of duodenum are then reconnected to form another anastomotic connection to the Roux limb at a location approximately 50–150 cm (1.6–4.9 ft) from the stoma, typically using a stapling instrument. It is at this connection that the digestive juices from the bypassed stomach, pancreas, gallbladder, and liver enter the jejunum or ileum to aid in the digesting of food. Due to the small size of the upper pouch, patients are forced to each at a slower rate and are satiated much more quickly, thereby reducing the caloric intake.

Because the food enters the intestines directly, conditions known as the "dumping syndrome" are created when certain types of "junk foods" are consumed (usually sweets and other simple carbohydrates). This creates unpleasant feelings of nausea, diarrhea, nervousness, and sweating, which in turn discourages patients from developing unhealthy eating patterns. With the RYGB procedure, a loss of at least 50% of excess body weight (EBW) is maintained in approximately 60% of patients at 5 years.

Aside from the RYGB procedure, another treatment which relates to the stomach is gastroesophageal reflux disease (GERD). The lower esophageal sphincter is located in a distal portion of the esophagus adjacent to the junction between the esophagus and the stomach. When food is digested, a properly functioning lower esophageal sphincter would allow food to pass from the esophagus to the stomach while preventing reverse flow. However, GERD is a disorder where the esophageal sphincter allows the stomach contents, which includes gastric acid and bile, to flow back into the distal portion of the esophagus. Some complications associated with GERD include heartburn, pulmonary disorders, chest pain, esophageal ulcers, esophagitis, Barrett's esophagus, and esophageal carcinoma.

Common treatments for GERD include the administration of prescription acid blockers. But these drugs afford only short term relief; additionally, these drugs can be expensive and may have long-term side effects. Surgical procedures have included a procedure called the Nissen fundoplication, where a portion of the gastric fundus is wrapped around the esophagus. The wrapped fundus applies pressure to the esophagus to limit the reverse flow of the stomach contents. Effectively elongating the esophagus by fundoplication or by extending it via a staple line may be done to treat GERD. Conventional fundoplication procedures may be effective at treating GERD, but they also have disadvantages. For instance, many of these procedures require large incisions to be made in a patient. Laparoscopic procedures typically require several smaller incisions formed in the abdominal wall for the insertion of instruments into the patient's body. However, such procedures can be expensive and they can increase the risks of post-operative hernias, accidental organ perforations, and other related drawbacks.

Treatments for the above-mentioned procedures, as well as others, typically require multiple tools to be inserted within the patient's body or require tools to be manipulated, advanced, or withdrawn from the body numerous times. Repeatedly treating a region of tissue may result in unintended damage to the surrounding tissue, and it may also make locating and relocating the region of tissue difficult each time a tool is withdrawn and relocated.

BRIEF SUMMARY OF THE INVENTION

In the treatment of hollow body organs, e.g., reducing the stomach size for the treatment of obesity, may involve, e.g., grasping the interior walls of the stomach and creating a stomach pouch by, e.g., stapling opposing sides of a stomach together to form two separate lumens from within the interior surface of the stomach. Accomplishing such treatments may require multiple passes through the esophagus by the tools used. An overtube assembly which is preferably comprised of an overtube member is disclosed which may be inserted into the hollow body organ, e.g., the stomach, through the esophagus of the patient.

The overtube may define a working lumen throughout which preferably. extends from the proximal end to the distal end of the overtube. At the distal end, at least one window, and preferably two or more windows may be defined opposite of one another. The windows are preferably defined in the shape of slots near or at the distal end of the overtube. The lengths and widths of these slots are preferably long enough to approximate a desired length of a boundary or junction line within the stomach. The slots are preferably located in apposition to one another, but other variations may include offset windows separated by a dividing wall within the overtube lumen, as well as windows which are both offset and alternating located in apposition to adjacent windows. The entire length of the overtube, or at least a majority of the length, is preferably flexible enough to be inserted within the body and conform to the curvatures within the body. Alternatively, the portions of the overtube length may be made to have different regions of flexibility. The overtube may also have a bendable region having a flexibility which enables it to be manipulated or bent into arbitrary shapes either actively by the physician or surgeon or passively by an endoscopic device inserted within the overtube.

A separate drive tube may be inserted within the overtube lumen and is preferably freely adjustable, i.e., longitudinally as well as rotationally within the overtube. The drive tube itself has a lumen defined within through which an endoscopic device may be inserted within to extend beyond the distal ends of both the overtube and the drive tube to examine and/or identify tissue regions of interest. A fastener is also preferably located within the lumen of the overtube and may be located distally of the drive tube. The proximal end of the fastener may be configured to engage the drive tube and may be formed into a variety of different shapes. For instance, the fastener may be in the form of a linear shape (e.g., in the form of a spear, harpoon, rivet, etc.), in a staple configuration, or in a spiral or helical shape having at least two revolutions. The shape of the fastener is generally determined, inter alia, by the desired approximated tissue configuration and the configuration of the overtube, as described in further detail below. It is also preferably configured to remain attached to the drive tube or to the inner wall of the overtube lumen until the fastener is deployed into the tissue region of interest. To deploy the fastener into the tissue, the drive tube with the fastener connected thereto may be advanced distally through the overtube lumen while rotating the drive tube via a proximally actuated torquing force. As the drive tube is rotated, the fastener is advanced into the tissue while fastening the tissue in a manner similar to a screw.

The overtube assembly may also comprise a fluid port which is in fluid communication with the working lumen of the overtube and which is also in fluid communication with a pump which may be used to provide negative pressure to create a vacuum within the overtube lumen; any number of ports may be used. Furthermore, the fluid port and any other fluid ports, if used, may also be fluidly connected to positive pressure pumps either in parallel or alternatively switched. Moreover, the same pump may be used to provide both negative and positive pressure.

In use, the overtube assembly may be inserted, e.g., orally, into a patient and advanced within the esophagus until the distal end is within the stomach. Once in the stomach, the distal end may be actively or passively positioned by the physician or surgeon until the device has been desirably positioned. The pump, which is preferably in fluid communication with the overtube lumen, may then be activated to create a vacuum within the overtube to draw portions of the identified tissue within the windows. Once the tissue has been adhered and drawn into the windows, the fastener or fasteners may be advanced into the invaginated tissue to secure it. If the procedure requires additional fasteners, the overtube device may be maintained in position within the stomach while the drive tube may be withdrawn from the region to position additional fasteners. Alternatively, the drive tube may be withdrawn or maintained in position and the endoscopic device may be removed from the overtube lumen to allow for the insertion of other tools or devices through the overtube into the region.

DETAILED DESCRIPTION OF THE INVENTION

Various tools and methods of treatment for hollow body organs, e.g., in the treatment of obesity, are described herein which are less traumatic and less invasive than procedures currently available. A variety of methods for such treatment of obesity, as well as other gastric-related diseases, e.g., gastroesophageal reflux disease (GERD), are disclosed. One method involves reducing the size of the stomach pouch through less invasive methods to limit the caloric intake as well as to provide an earlier feeling of satiety. This may be done by creating a smaller gastric pouch within the stomach which significantly limits the amount of food which may be ingested.

In reducing the stomach size, one variation involves grasping the interior walls of the stomach via the overtube device described herein and creating the stomach pouch with the overtube using a variety of devices and methods, e.g., stapling opposing sides of a stomach together to form two separate lumens from within the interior surface of the stomach. Alternatively, a separate endoscopic stapling device may be inserted within the overtube to accomplish such a task. Such an endoscopic stapler could be inserted separately within the overtube to apply a fastening element, e.g., staples, clips, tags, screws, etc., into two regions of apposed tissue drawn within the overtube to affix them together.

Figure 1A:
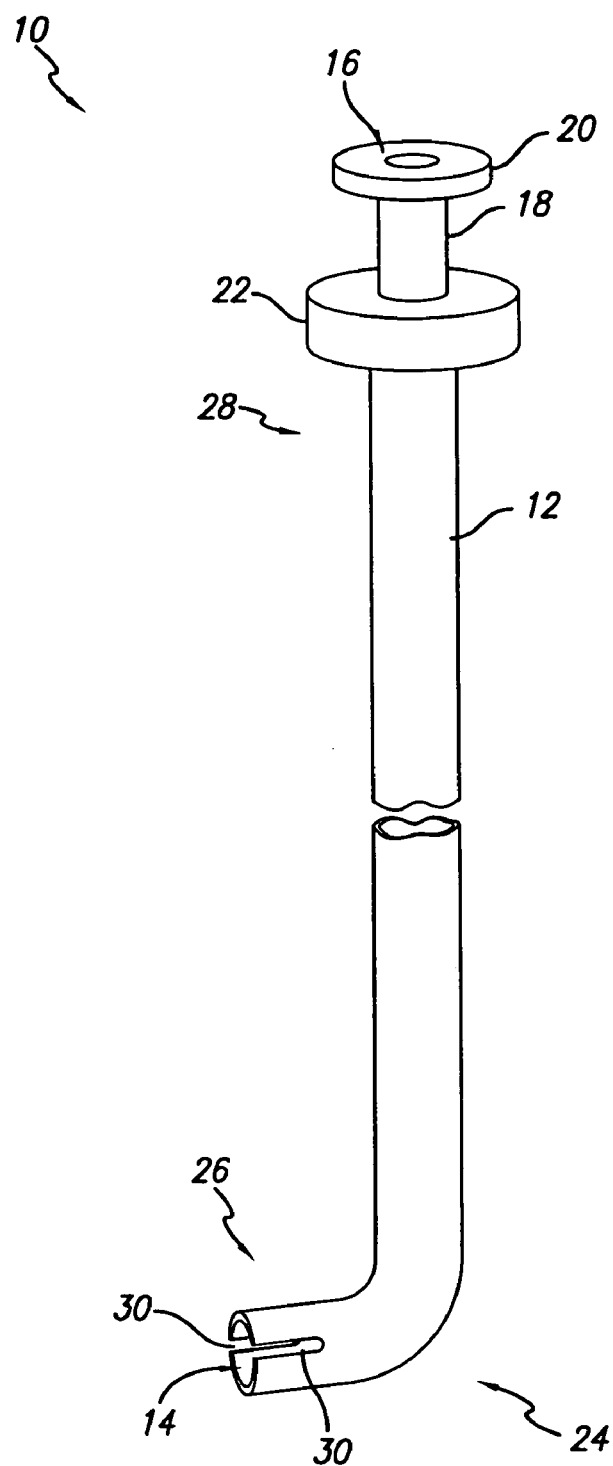
FIG. 1A shows an isometric view of an overtube assembly having a bendable distal region.

Treating a hollow body organ may require multiple passes by the tools used, and FIG. 1A shows an isometric view of overtube assembly 10 which can be used to efficiently affect treatment with minimal discomfort to a patient. Overtube assembly 10 is preferably comprised of overtube member 12 which may be inserted into the hollow body organ, e.g., the stomach, through the esophagus of the patient. A working lumen 14 may be defined through overtube 12 from proximal end 28 at overtube module 22 to distal end 26 of overtube 12. At distal end 26, at least one window 30, and preferably two or more windows 30 are preferably defined opposite of one another in this variation, as shown. Windows 30 are preferably defined in the shape of slots near or at the distal end 26 of overtube 12. The lengths and widths of slots 30 may vary and are preferably long enough to approximate a desired length of a boundary or junction line within the stomach, as discussed below. The stomach is comprised of at least three layers including the inner mucosal layer (mucosa), a muscular layer exterior to the mucosa (muscularis mucosae), and an exterior serosal layer (serosa). The widths of window 30 are preferably wide enough to accommodate at least two layers of the stomach interior lining and more preferably all the layers of the stomach. Illustrative widths of window 30 may range anywhere from about 0.320 cm (0.125 in.) to 0.950 cm (0.375 in.) and may range anywhere in length from about 0.635 cm (0.250 in.) to 15.25 cm (6 in.). Overtube assembly 10, including the variations described herein, may be used to effect a variety of treatments in combination with a variety of tools and methods. Some of the tools and methods with which assembly 10 may be used are described in detail in commonly owned and co-pending U.S. patent application Ser. No. 09/871,297 filed May 30, 2001 and which has been incorporated above by reference in its entirety.

Several aspects of the present invention were arrived at after experimentation with stomach tissue and the challenges of acquiring and securing such tissue reliably. In particular, it is desirable that the assembly 10 consistently approximate the tissue such that when fasteners are delivered, as described herein, they consistently reach the outer layers, or fibrous layers, of the stomach wall, such as the muscularis and serosa. The present invention may assist in this by acquiring tissue such that these fibrous layers intersect or overlap within working lumen 14, allowing them to be secured together. Once these fibrous layers are fastened appropriately, they will adhere, fuse, or scar over to affect the desired fastening. The tissue is preferably maintained in apposition with, e.g., the two folds, for 2–4 weeks to affect healing, but that fusion of the tissue may take place as soon as 5–10 days following a procedure. If tissue folds are fastened inconsistently, or if the fasteners only penetrates the less fibrous tissue, such as the mucosa, complications such as gastric erosion, ulceration, and failure of the secured walls may result.

The entire length of overtube 12, or at least a majority of the length of the device, is preferably flexible enough to be inserted within the body through, e.g., the esophagus, and conform at least partially to the curvatures within the body. For example, overtube 12 may range in length from about 40 cm (15.75 in.) to 100 cm (39.40 in.), and is preferably about 80 cm (31.50 in.). The overall diameter of overtube 12 may range from about 5 mm (0.20 in.) to 30 mm (1.18 in.), and preferably from about 15 mm (0.60 in.) to 17 mm (0.70 in.). Alternatively, the length of overtube 12 may be sufficiently flexible yet define a bendable region 24 near distal end 26 which may be more flexible than the rest of overtube 12. Bendable region 24 may have a flexibility such that it may be manipulated or bent in arbitrary shapes either actively by the physician or surgeon or passively by an endoscopic device inserted within overtube 12. Examples of tubular structures which are actively manipulatable and selectively rigidizable may include those found in U.S. Pat. No. 5,624,381 (Kieturakis) and U.S. Pat. No. 4,790,294 (Allred, III et al.), among others.

Figure 1B:
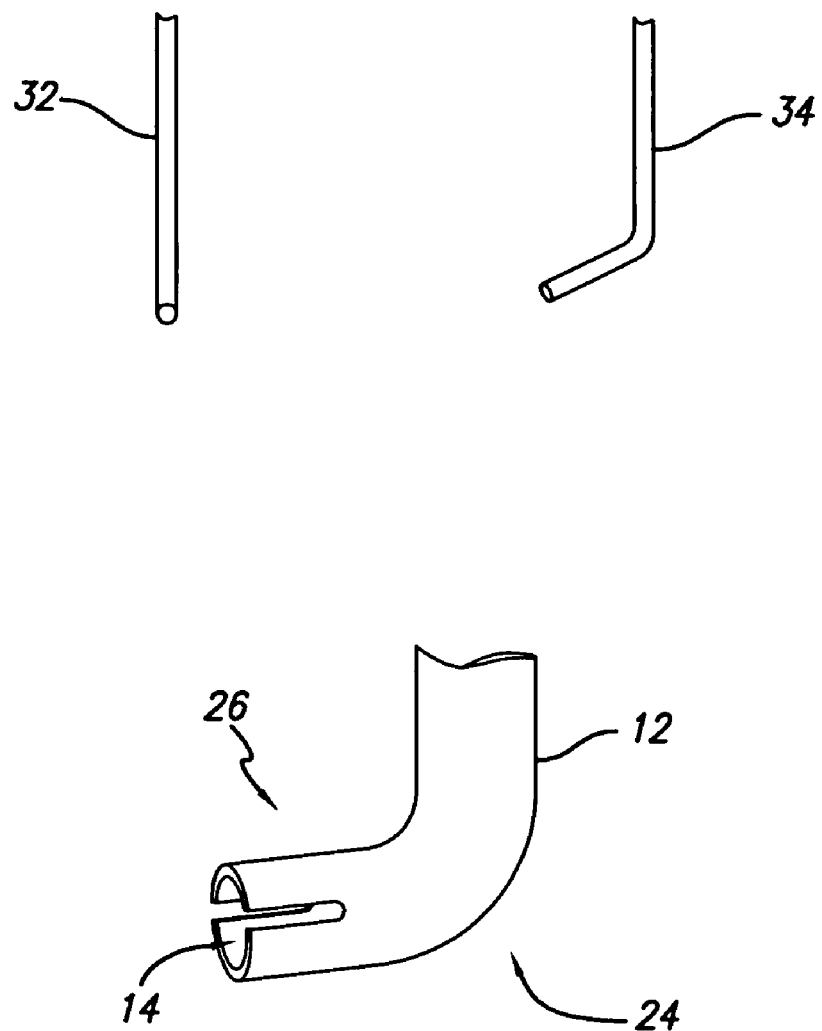
FIG. 1B shows optional shaping mandrels which may be inserted through or along the overtube assembly.

If passively manipulatable, overtube 12 may be made from any variety of biocompatible materials which provide sufficient structure to the device yet allows for the device to be bent, e.g., thermoset or thermoplastic materials such as PTFE, FEP, polyurethane, PVC, silicone, Nylon, pellethane, etc. Alternatively, overtube 12 may be preformed to have a bent or arcuate configuration near or at distal end 26. When inserted into a patient, a straightening mandrel 32 or endoscopic device may be positioned within the curved region 24 to maintain a straightened configuration, as shown in FIG. 1B. When overtube 12 has been desirably positioned within the patient, the straightening mandrel 32 may be withdrawn from the device leaving the overtube 12 to reconfigure itself to its preformed shape. Another alternative is to have overtube 12 remain passively manipulatable and to have the insertable mandrel preformed into the curved configuration 34, as also seen in FIG. 1B. In this case, the overtube 12 may be inserted in its straightened configuration and the curved mandrel 34 may be inserted through the overtube 12 in a constrained and straightened configuration through overtube 12. When curved mandrel 34 reaches the distal end 26, mandrel 34 may be allowed to curve into its preformed shape which may force overtube 12 to reconfigure with the mandrel 34. The mandrel 34, in this case, is preferably made of a shape memory alloy, e.g., a nickel-titanium alloy such as Nitinol. In either case, the mandrel may be inserted within an internal working channel of overtube 12 or along a exterior channel defined along the outer surface of overtube 12.

Overtube 12 may also be made to have a proximal portion which is relatively stiffer than bendable region 24 or distal end 26. Also, overtube 12 may have a wall thickness which depends upon the type of material used for construction which is sufficient to maintain the structural integrity of the device during use. For example, a wall thickness ranging from about 0.80 mm (0.032 in.) to 6.35 mm (0.250 in.) may be used.

A separate drive tube 18 is preferably inserted within lumen 14 of overtube 12 through overtube module 22. Drive tube 18 is preferably a tubular member which has an outer diameter which is smaller than the inner diameter of overtube 12. Drive tube 18 may be fabricated from the same or a similar material as overtube 12 or any of the other materials described above. There is preferably enough clearance between tubes 12, 18 such that drive tube 18 is freely adjustable within overtube 12, i.e., freely movable longitudinally and/or rotationally within overtube 12. Drive tube 18 is made to have a lumen defined through the tube 18 from a proximally located insertion port 16 to the distal end of tube 18. To prevent drive tube 18 from being pushed entirely through overtube 12, drive tube stop 20 may be located at the proximal end of tube 18. Stop 20 may be any projection, e.g., an enlarged diameter disk, which abuts against overtube module 22 to prevent the further advancement of drive tube 18 within overtube 12. Stop 20 may be made from a material similar to tube 18 or it may be made from a biocompatible metallic material such as stainless steel, platinum, etc., and attached to drive tube 18.

Figure 2:
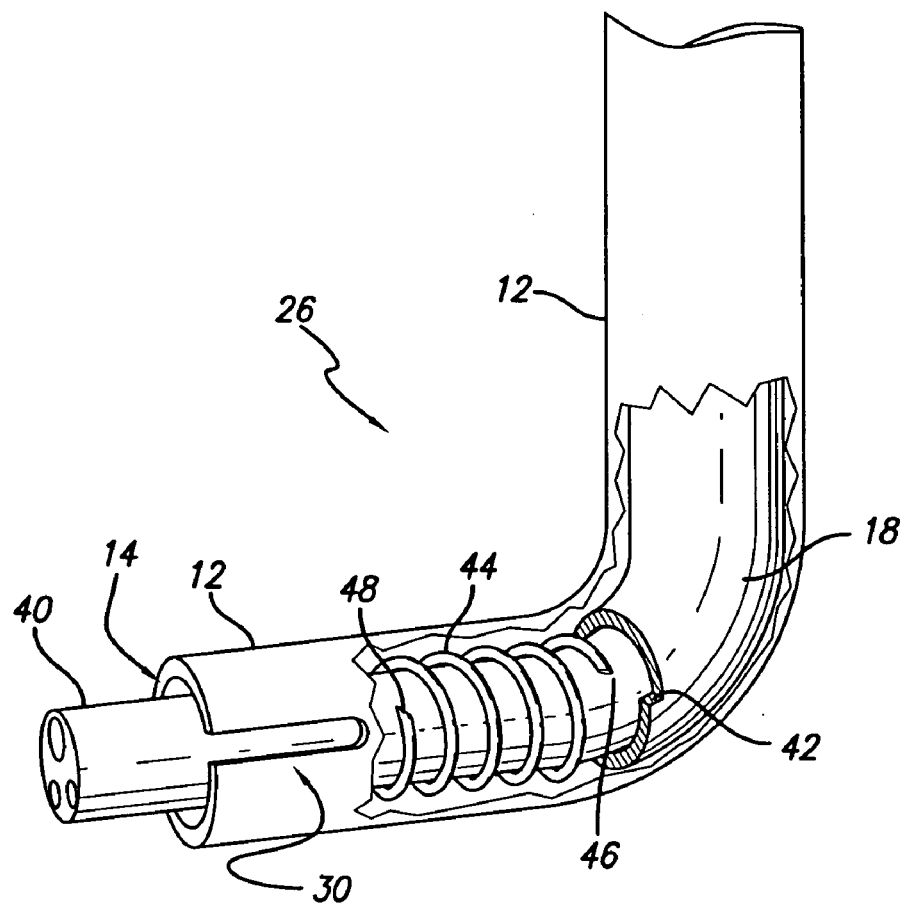
FIG. 2 shows a detailed assembly view of a variation on the distal end of the overtube assembly showing a fastener and a drive tube positioned within the overtube.

A detailed assembly view of the distal end 26 of overtube assembly 10 is shown in FIG. 2 with the wall of overtube 12 partially removed for clarity. As shown, overtube 12 may have drive tube 18 inserted within lumen 14 and extending towards the distal end of overtube 12. An endoscope 40, which may comprise any conventional endoscopic device preferably having optical viewing capabilities (e.g., through optical fibers), may be inserted within drive tube 18 at its proximal end through insertion port 16. Endoscope 40 may be advanced distally through both overtube 12 and drive tube 18 to extend beyond the distal end 26 of overtube 12 to examine and/or identify tissue regions of interest.

Also preferably located within lumen 14 near or within the distal end 26 of overtube 12 is fastener 44. Fastener 44 is preferably located distally of drive tube 18 and may be configured to have a proximal end 46 for engagement with fastener engagement area 42 of drive tube 18. It may be further configured to have a tapered distal tip 48 for piercing tissue as fastener 44 is advanced distally. As shown, fastener 44 may be configured in a spiral or helical shape having at least two revolutions and it may be configured to form an inner diameter which is large enough to allow endoscope 40 to pass therethrough uninhibited. During advancement of overtube 12 into the body or during examination of the tissue with endoscope 40, fastener 44 may be maintained within lumen 14 by some temporary attachment device against the inner wall of lumen 14. Preferably, however, fastener 44 may be attached via proximal end 46 to area 42 until fastener 44 is deployed into the tissue. Proximal end 46 may be temporarily connected to area 42 via a conventional mechanical engagement, such as a friction fit or a detente located within area 42, or via an electrically-actuated joint or connection, e.g., an electrically-erodable joint.

Once fastener 44 is to be deployed into the tissue, drive tube 18 with fastener 44 connected thereto, may be advanced distally through lumen 14 and drive tube 18 may then be rotated via a proximally actuated torquing force. The torquing force may be actuated either manually or automatically with a motorized assembly (not shown). As drive tube 18 rotates about its longitudinal axis, fastener 44 also rotates and advances into the tissue region of interest while fastening the tissue in a manner similar to a screw.

Fastener 44, which is preferably in the shape of a helix or spiral, may optionally have a tapering width or diameter. The first few turns or coils of fastener 44 may have the same or similar diameter than the remaining tapering coils; this may enable distal piercing end 48 to engage the tissue and may also allow fastener 44 to be advanced at the desired orientation through the tissue. Fastener 44 preferably maintains a parallel orientation with overtube 12 during delivery into the tissue, i.e., a longitudinal axis defined by fastener 44 is preferably parallel, or close to parallel, with the longitudinal axis defined by overtube 12. Moreover, the outer diameter of the first few turns or coils may be the same diameter, or slightly less than, the inner diameter of overtube 12. This may further enable fastener 44 to be advanced through lumen 14 at the proper orientation prior to engaging the tissue.

Fastener 44 may be made of a bioabsorbable or biocompatible material, as described herein such as a polymer or superelastic alloy, or a metal, e.g., stainless steel, platinum, titanium, etc., and may be integrally formed with barbs or whisker-like filaments protruding along its length to help prevent fastener 44 from backing out once it has been engaged within the tissue. An example of a spiraling suturing needle or fastener which may be used in this variation is shown and described in U.S. Pat. No. 5,330,503 to Yoon, which is incorporated herein by reference in its entirety.

Figure 3A:
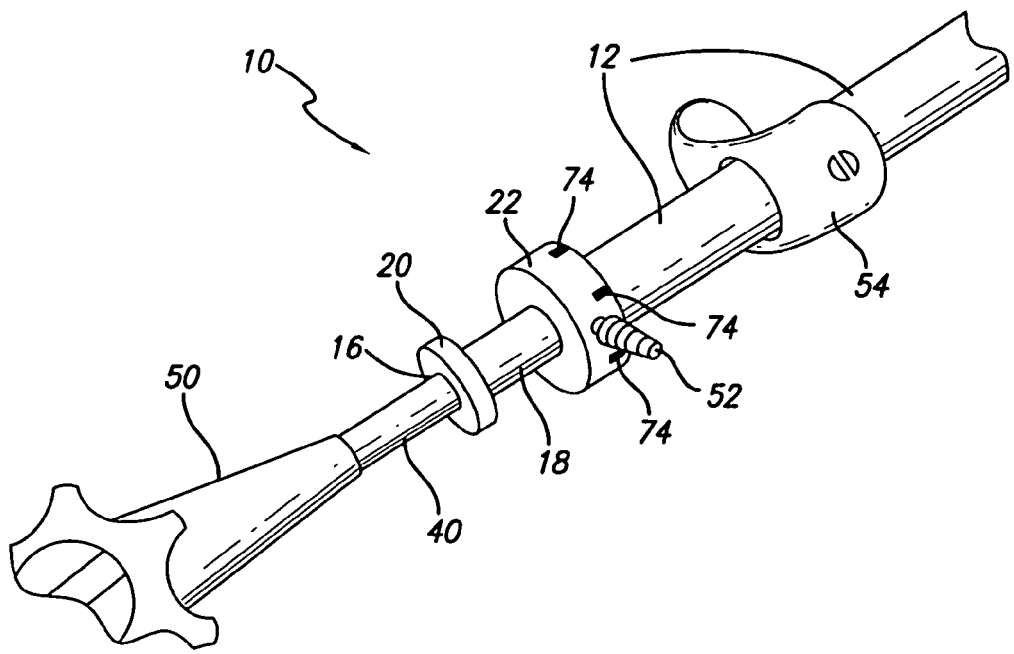
FIG. 3A shows a detailed isometric view of the proximal assembly of the overtube.

FIG. 3A shows a detailed isometric view of the proximal assembly of overtube assembly 10 with endoscope 40 inserted within insertion port 16. The shaft of endoscope 40 may be seen almost fully inserted within assembly 10 up to endoscope handle 50 through insertion port 16 located in drive tube stop 20. Endoscope 40 may be selectively advanced and withdrawn by the physician or surgeon into assembly 10 or it may be withdrawn completely from insertion port 16 during a procedure to allow for the insertion of other tools or devices.

Also seen extending from overtube module 22 is fluid port 52 which may be included as part of overtube assembly 10. Fluid port 52 is a port which is in fluid communication with working lumen 14 defined within overtube 12 and may be in fluid communication through, e.g., a hose, to a pump which may provide the negative pressure to create a vacuum within lumen 14. Although a single fluid port 52 is shown, any number of ports may be used. If multiple ports are utilized, each port may be fluidly connected to the same or a different pump. Furthermore, fluid port 52 and any of the other fluid ports, if used, may also be fluidly connected to positive pressure pumps either in parallel or alternatively switched. Alternatively, the same pump may be used to provide both negative and positive pressure. Positive pressure pumps may be used to provide the adequate pressure to deliver fluids through fluid port 52 into lumen 14 for delivery of, e.g., therapeutic drugs, saline, or gases such as nitrogen for insufflating an area within the body, among other fluids.

Any number of markers 74 may be placed upon the overtube assembly 10, e.g., upon overtube module 22 as shown in FIG. 3A. Markers 74 may be placed upon module 22 to correspond with the circumferential location of windows 30 and may thus be used as a guide for aligning windows 30 within the patient. Overtube 12 may be manipulated and rotated from outside the body to align markers 74 with a landmark located on the patient, e.g, alignment with the patient's nose. In this manner, windows 30 of overtube 12 may be desirably positioned within the patient through external manipulation without the need to align windows 30 by direct visualization within the patient.

Figure 3B:
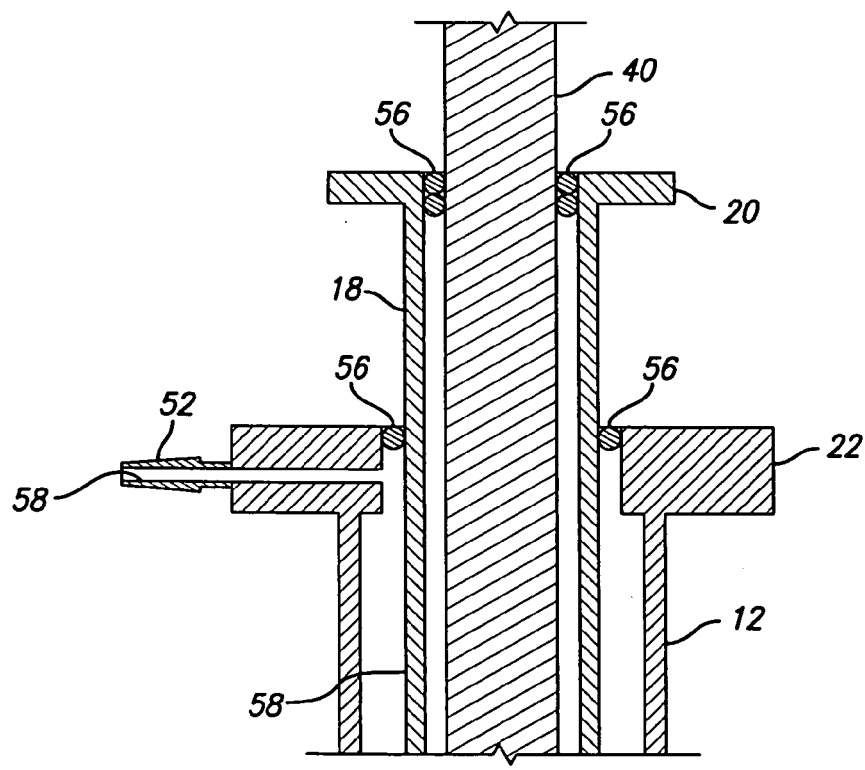
FIG. 3B shows a cross-sectioned profile of the assembly of FIG. 3A.

As drive tube 18 may be selectively advanced and withdrawn relative to overtube 12 and also relative to endoscope 40, a fluid-tight seal is preferably maintained between overtube module 22 and drive tube 18. This fluid-tight seal is preferably sustained in order to maintain the pressure (positive or negative pressure) within lumen 14 through fluid port 52, and more specifically within the communication lumen 58 which is created between the outer surface of drive tube 18 and the inner surface of overtube 12, as seen in FIG. 3B, which shows a cross-sectioned profile of the assembly of FIG. 3A. and may be accomplished by any number of conventional sealing methods. For instance, overtube module 22 may be gasketed 56 against the outer surface of drive tube 18 to maintain the seal between the two, as also seen in FIG. 3B. Alternatively, other types of seals using, e.g., sealing gels, ferrofluidic seals, etc., may be utilized. In addition to maintaining fluid-tight seals, guard 54 may also be included in assembly 10 to provide structural strength to the area of tissue through which assembly 10 is inserted and also to prevent overtube 12 from being pinched or crushed. For instance, if assembly 10 were inserted orally into the esophagus of a patient, guard 54 may be inserted into the mouth of the patient and used as a bite guard to prevent the patient from biting down on overtube 12. Also, guard 54 would also ensure a smooth pathway for overtube 12 through the mouth of the patient.

Figure 4:
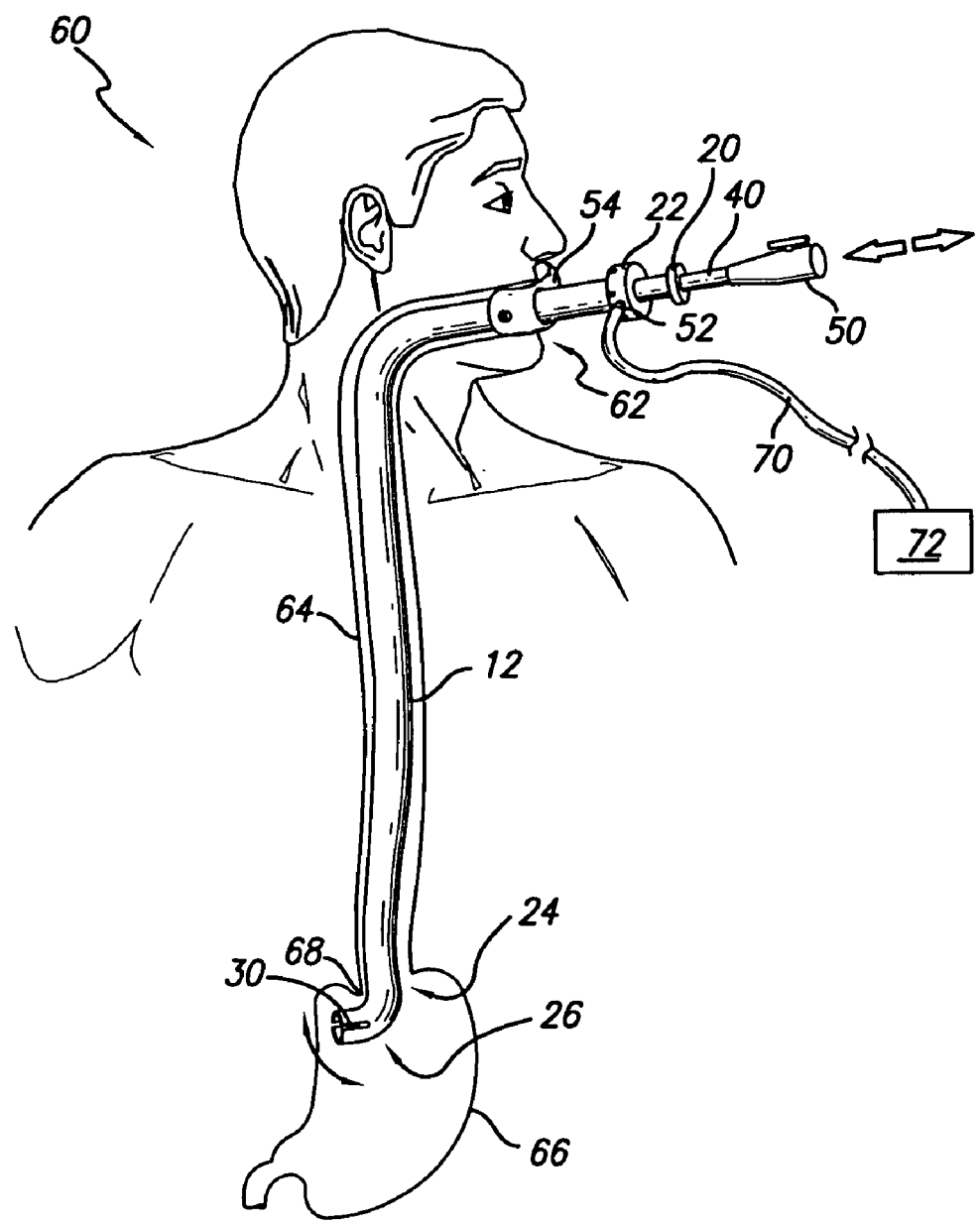
FIG. 4 shows a schematic of one example of the overtube assembly in use within a patient.

FIG. 4 shows a schematic of one example of assembly 10 in use within a patient 60. As shown, assembly 10 may be inserted orally through mouth 62 of patient 60 and advanced within esophagus 64 until distal end 26 is advanced beyond gastroesophageal junction 68 and into stomach 66. Once in stomach 66, distal end 26 may be actively or passively positioned by the physician or surgeon about bendable region 24 until the device has been desirably positioned. Then pump 72, which is preferably in fluid communication with communication lumen 58 within overtube 12 through fluid tube 70, may be activated to create a vacuum within overtube 12 to draw portions of the identified tissue within windows 30. A vacuum force of about 15 to 20 inch-Hg may be utilized, although the amount of vacuum pressure may be varied depending upon the size of the windows 30 and the amount of tissue to be drawn into overtube 12. As mentioned above, pump 72 may also be used as a positive pressure pump which may then be used to deliver therapeutic agents, fluids, or gases through tube 70 and overtube 12 for dispersion within stomach 66.

Figure 5:
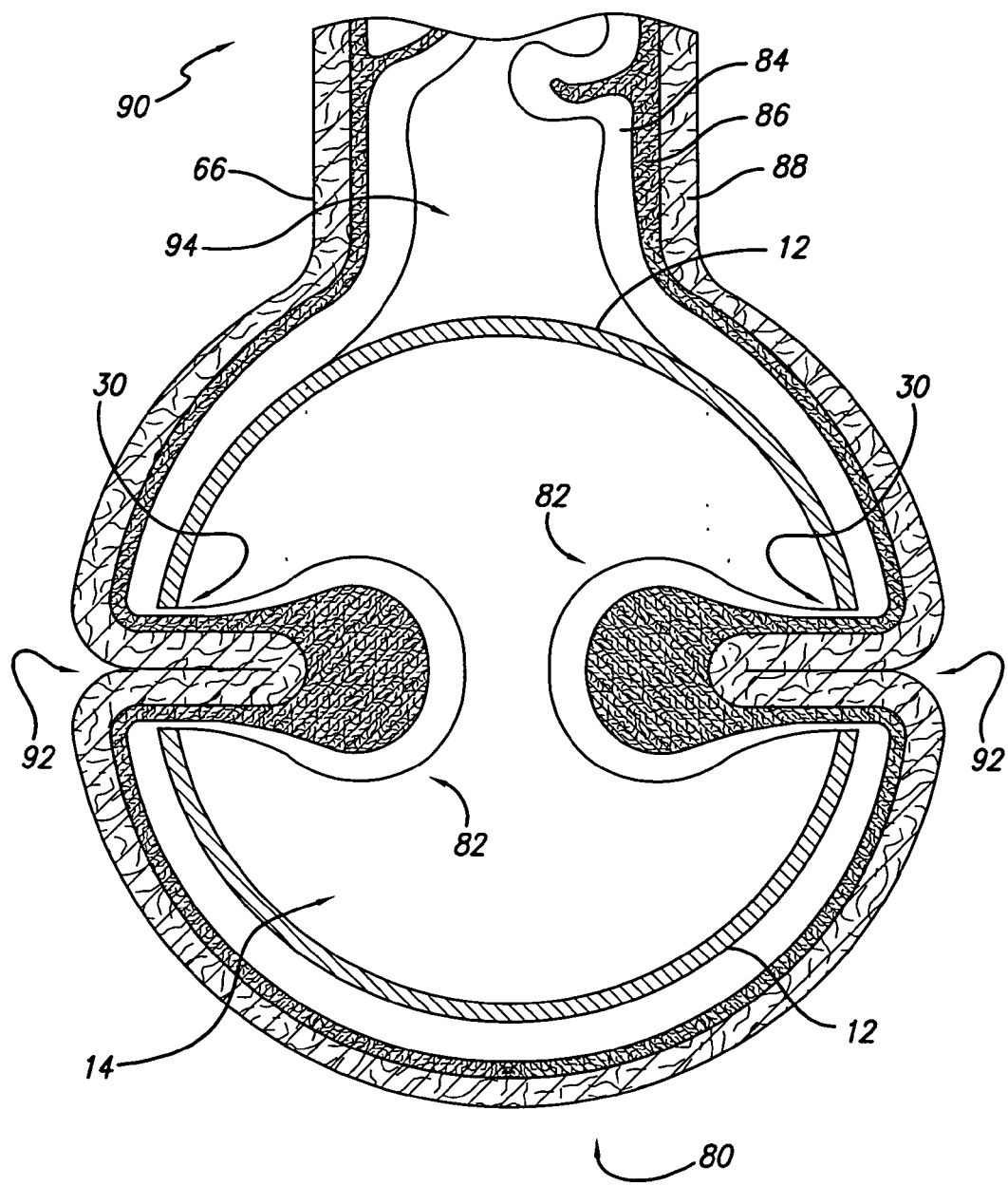
FIG. 5 shows a cross-sectioned end view of the overtube in use within a stomach lumen.

FIG. 5 shows a cross-sectioned end view of overtube 12 within stomach lumen 94 of stomach 66 once the vacuum has been created within working lumen 14. As shown, overtube 12 may be positioned adjacent relative to lesser curvature 80 of stomach 66; however, overtube 12 may alternatively be positioned closer to greater curvature 90 or anywhere in between depending upon the desired treatment and effects upon the patient. For instance, overtube 12 is preferably positioned closer to lesser curvature 80 prior to approximating the walls of stomach tissue such that a modified lumen may be created by overtube assembly 10 leading directly from esophagus 64 to the pyloral sphincter of stomach 66. Alternatively, overtube 12 may be positioned closer to greater curvature 90 for the treatment of GERDs. As seen, overtube 12 may acquire the lining of the stomach and draw several layers of stomach tissue, i.e., mucosal layer 84, muscular layer 86, and serosal layer 88, into lumen 14 through windows 30 while creating creases 92 within the outer surface of stomach 66 which may denote where stomach 66 has been invaginated. All the layers of stomach 66 need not be invaginated, but at least two layers are preferably drawn in, and more preferably all the layers, so that adequate tissue exists within lumen 14 for approximating the walls of stomach 66. The vacuum is preferably maintained until the invaginated tissue 82 is drawn within lumen 14 such that a fastener, as described further below, may grasp both, or several, regions of invaginated tissue 82 and approximate or maintain the tissue.

Figure 6:
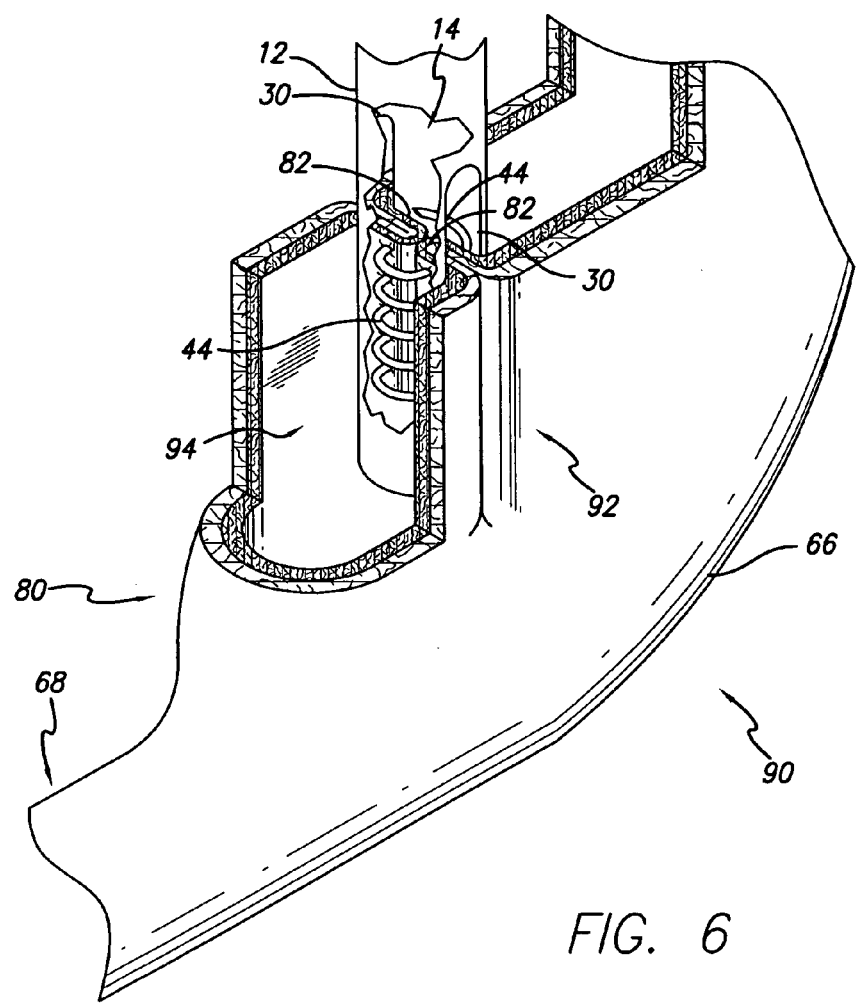
FIG. 6 shows an isometric view of the overtube within a stomach with the stomach and overtube walls partially removed for clarity.

FIG. 6 shows an isometric view of overtube 12 within stomach 66 with the stomach and overtube walls partially removed for clarity. As shown, overtube 12 may be inserted, as described above. Once desirably positioned within stomach lumen 94, a vacuum may be created within working lumen 14 of overtube 12 and tissue 82 may become invaginated within lumen 14 through windows 30, as shown. Once the invaginated tissue 82 has been adequately drawn into overtube 12, any number of flexible endoscopic stapling devices may be used to hold the suctioned tissue together. Such stapling devices may include any of the devices as discussed in further detail in U.S. patent application Ser. No. 09/871,297 which has been incorporated herein, as above.

Alternatively, fastener 44 may be advanced distally while rotating it using drive tube 18, which is shown as having been withdrawn. As fastener 44 is rotatingly advanced, its piercing distal tip 48 may wind into and around invaginated tissue 82 in an alternating helical or spiral pattern until fastener 44 has been filly advanced into tissue 82. Fastener 44 may be configured to have an inward bias such that once fastener 44 has been deployed within tissue 82, the coils of fastener 44 bias inwardly such that the fastener 44 diameter shrinks and fastener 44 elongates. A single fastener 44 may be used to bind the apposing walls of tissue 82 within stomach 66, in which case fastener 44 is preferably an elongated fastener sufficiently long enough to bind the tissue. Alternatively, multiple fasteners 44 may be fastened one after another to form a continuous fixation line. In which case overtube 12 may be advanced to a distal position within stomach 66 and a portion of the tissue walls may be fastened, as described above. Overtube 12 may then be pulled proximally a short distance within stomach lumen 94 and repositioned.

While maintaining the position of overtube 12 within stomach lumen 94, drive tube 18 may be withdrawn from overtube lumen 14 and another fastener 44 may be inserted within overtube 12 and advanced distally to fasten another portion of the tissue wall. This process may be repeated as necessary until the desired length or locations of tissue have been fastened. An alternative configuration for the drive tube may include a clamping device for holding the approximated tissue to one another while fastening the tissue together, as discussed in further detail below.

A biodegradable plug may optionally be placed into the distal end of overtube 12 prior to insertion into the patient and is preferably made of a biocompatible biodegradable material, e.g., biodegradable polymers such as polylactide, polyglycolide, and their copolymers. The plug may be alternatively made from a non-biodegradable material and may simply pass after the procedure. The plug may aid in maintaining a vacuum seal through windows 30 during the fastening procedure.

Figure 7A:
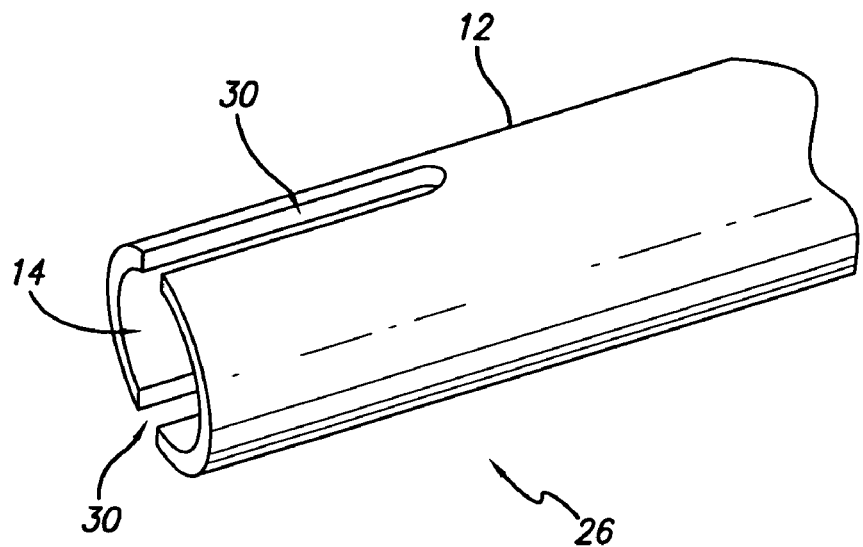
FIGS. 7A and 7B show isometric and end views, respectively, of one variation of the overtube distal end.
Figure 7B:
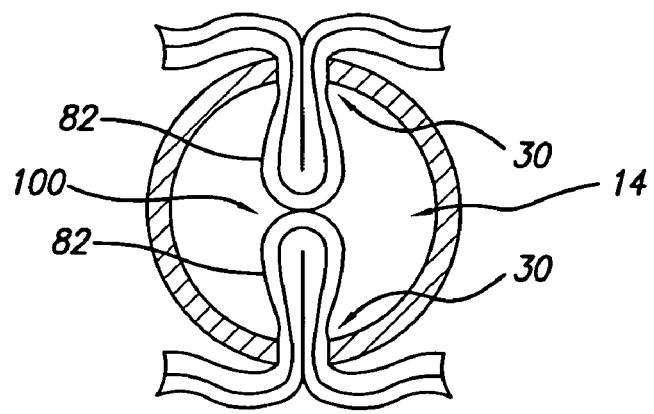

FIGS. 7A and 7B show detailed isometric and end views of one variation of distal end 26 of overtube 12. As shown in FIG. 7A, windows 30 may be formed into slots. FIG. 7B shows an end view with invaginated tissue 82 projecting into lumen 14. The apposed portions of tissue 82 may be drawn into overtube 12 via a vacuum force until the tissue 82 portions contact one another at contact area 100.

Figure 8A:
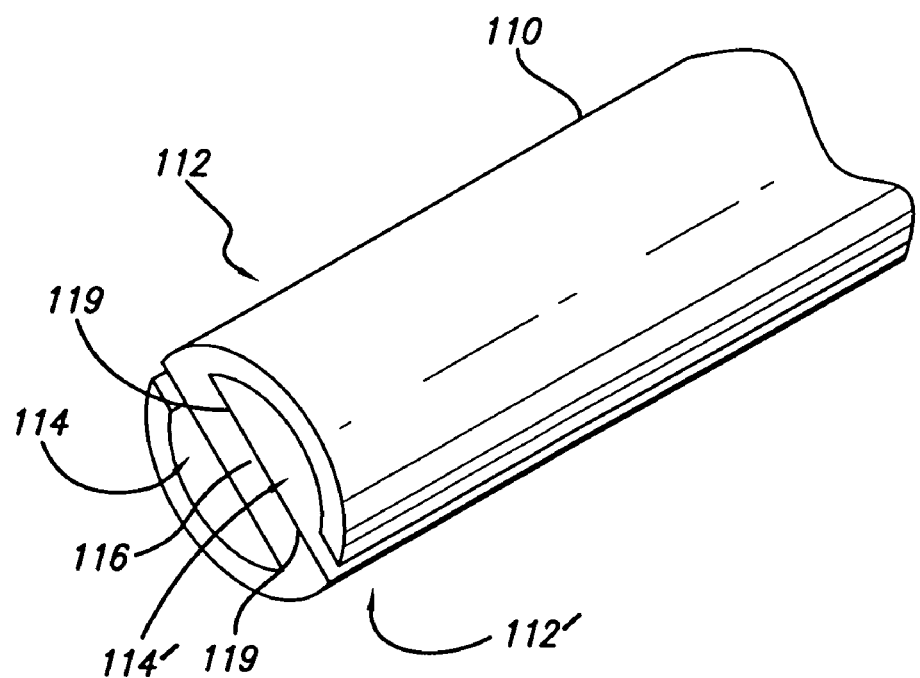
FIGS. 8A and 8B show isometric and end views, respectively, of another variation of the overtube distal end having offset windows.
Figure 8B:
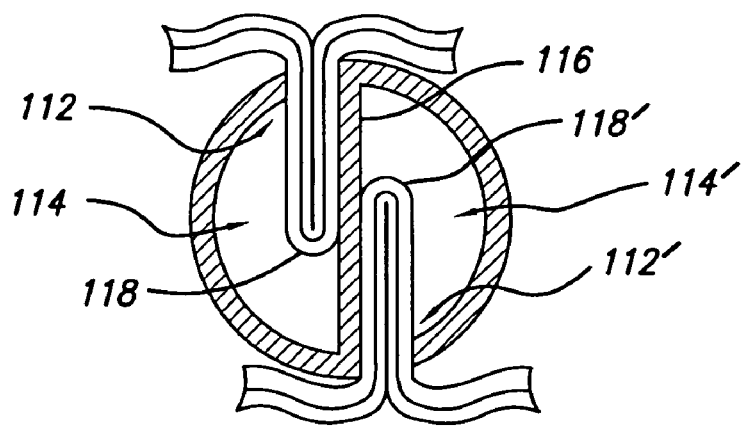

Another variation for configuring the distal end of the overtube is shown in FIGS. 8A and 8B. As seen in FIG. 8A, an isometric view of overtube offset variation 110 may have the apposed windows 112, 112' defined along the length of overtube 110 near or at the distal end, as described above. However, the working lumen within overtube 110 may have dividing wall 116 formed within and extending diametrically to form two separate lumens 114, 114'. Dividing wall 116 is preferably formed within the distal end portion of overtube 110 and may be as long as windows 112, 112'. Alternatively, wall 116 may extend throughout the length of overtube 110. Each separated lumen 114, 114' may open to a window 112, 112', respectively. As shown in FIG. 8B, apposed walls of tissue 118, 118' maybe drawn into respective lumens 114, 114' until they overlap one another between dividing wall 116. To fasten and/or approximate the apposed walls of tissue 118, 118', an endoscope or flexible fastening device may be used to fasten the tissue to one another. Alternatively, longitudinally-shaped channels 119 may optionally be defined within wall 116 near where dividing wall 116 joins overtube 110 wall. A helically or spirally-shaped fastener, as described above, may then be used with this variation as well. This variation 110 may or may not be used with a separate endoscope disposed within the working lumen.

Figure 9A:
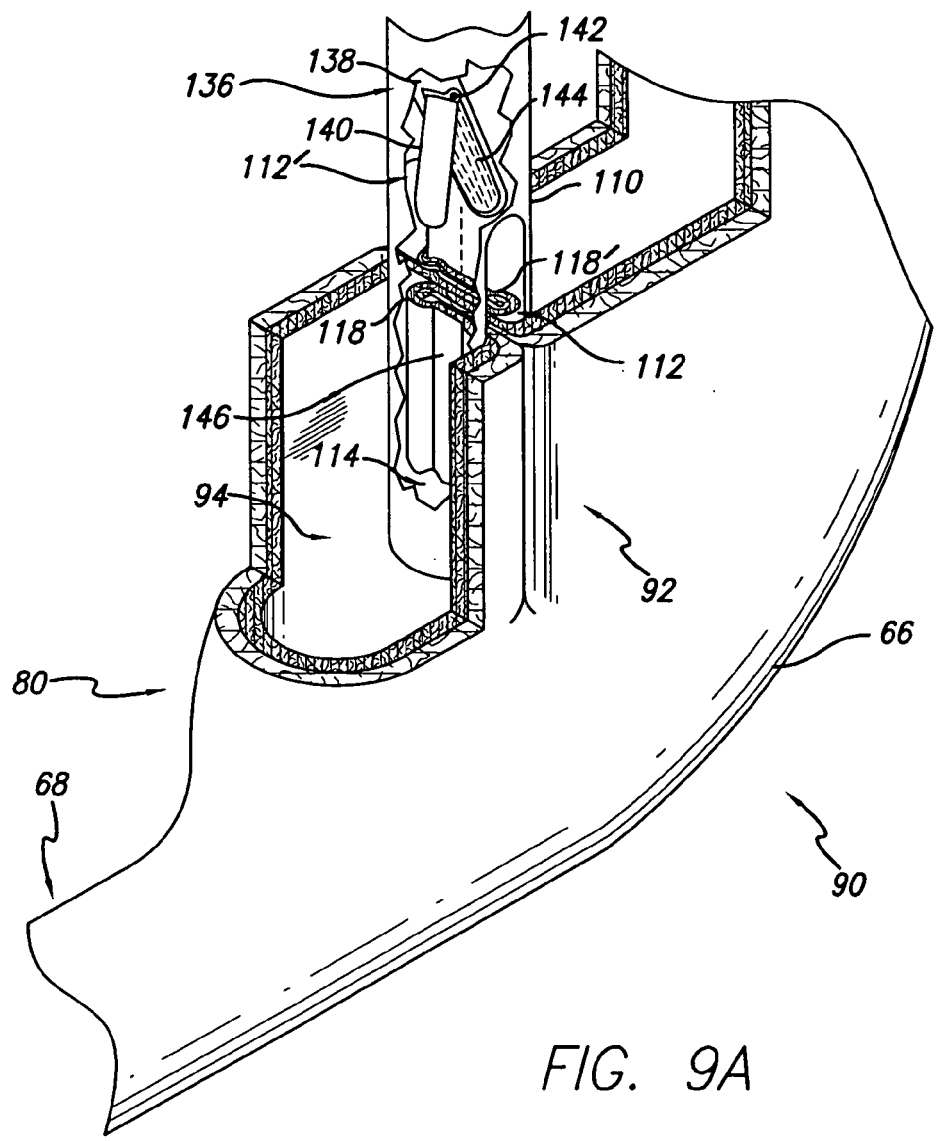
FIGS. 9A and 9B show isometric views of an overtube variation within a stomach prior to tissue fixation and after, respectively.
Figure 9B:
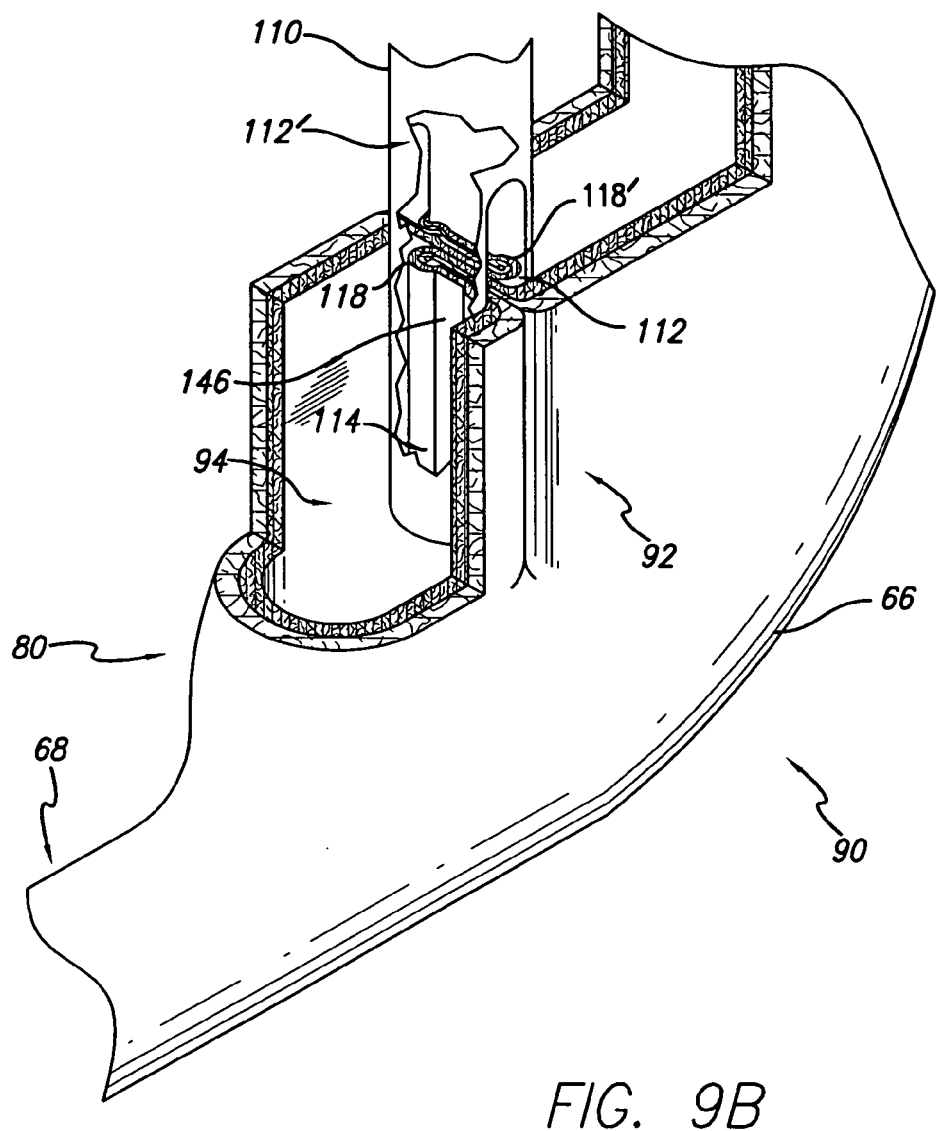

FIG. 9A shows an isometric view of overtube variation 110 inserted within stomach lumen 94 with the walls of both stomach 66 and overtube 110 partially removed for clarity. As shown, the invaginated and overlapping stomach lining 118, 118' can be seen within first and second lumen 114, 114' (dividing wall 116 has been removed for clarity only). As the overlapping tissue 118, 118' is held relative to one another, fastening assembly 136 may be advanced within overtube 110 to where the approximated tissue is positioned. Fastening assembly 136 may be any one of the fastening devices or endoscopic stapling assemblies as described above. The example shown comprises shaft 138 with fastening anvil 140 pivotally attached about pivot 142. Fastening assembly 136 may be manipulated from its proximal end to clamp the tissue 118, 118' between anvil 140 and fasteners 144. As described above, fasteners 144 may be in the form of staples, rivets, or other mechanical fasteners which may be housed within shaft 138. To secure the tissue to one another, fastening assembly 136 may be clamped onto overlapping tissue 118, 118' to create a fixation zone or region 146. FIG. 9B shows tissue 118, 118' having been attached together over fixation region 146 and fastening assembly 136 having been withdrawn from overtube 110.

Figures 10A, 10B:
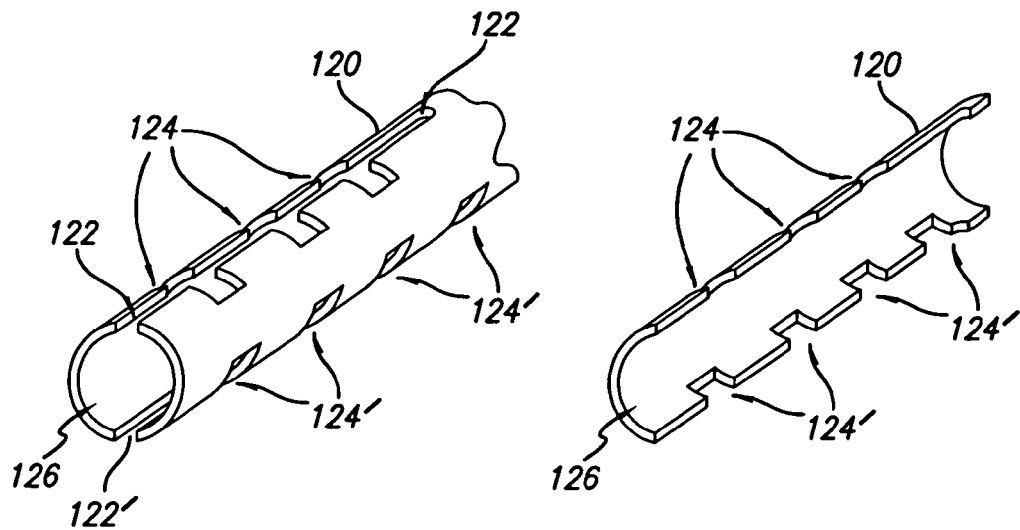
FIGS. 10A and 10B show isometric views of another variation of the overtube distal end having alternating windows.
Figure 11A:
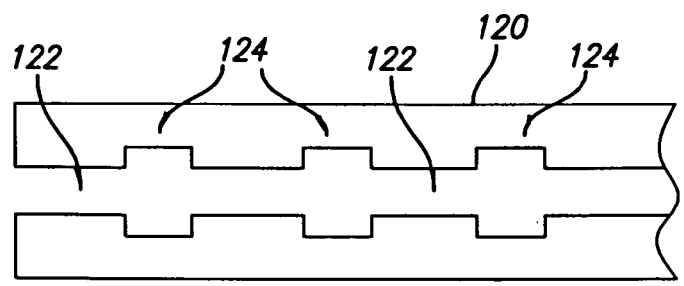
FIGS. 11A and 11B show side views of the overtube of FIGS. 10A and 10B.
Figure 11B:
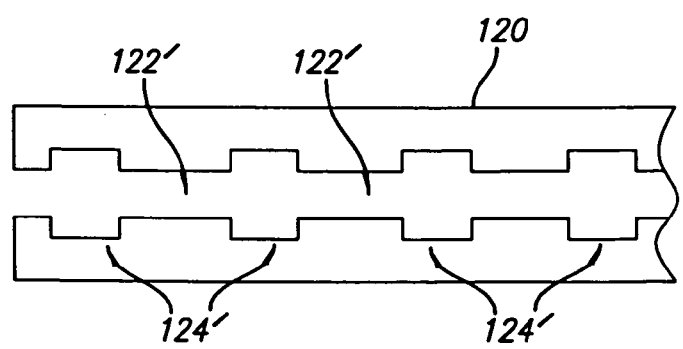

FIGS. 10A to 11B show another variation for configuring the distal end of the overtube. FIG. 10A shows an isometric view of overtube 120 which has several alternating windows. On apposing sides of overtube 120, first channel 122 and second channel 122' may be defined extending longitudinally along the distal end of overtube 120. Along first channel 122, a number of windows 124 may be defined which are preferably evenly spaced from one another with first channel 122 running throughout. On the apposed side, second channel 122' may be defined with a number of windows 124' which are also evenly spaced from one another. Windows 124 and 124' may be similarly shaped but are preferably alternating with apposed windows to allow tissue to be drawn within lumen 126 in an overlapping manner. FIG. 10B shows an isometric view of the overtube 120 from FIG. 10A with half the wall removed for clarity. FIG. 11A shows a side view of overtube 120 and first channel 122 while FIG. 11B shows a side view of the other side of overtube 120 and second channel 122'. The number of windows in either channel 122, 122' is not intended to be limiting but any number of alternating windows may be incorporated within overtube 120 depending upon the desired application and results.

Figure 12:
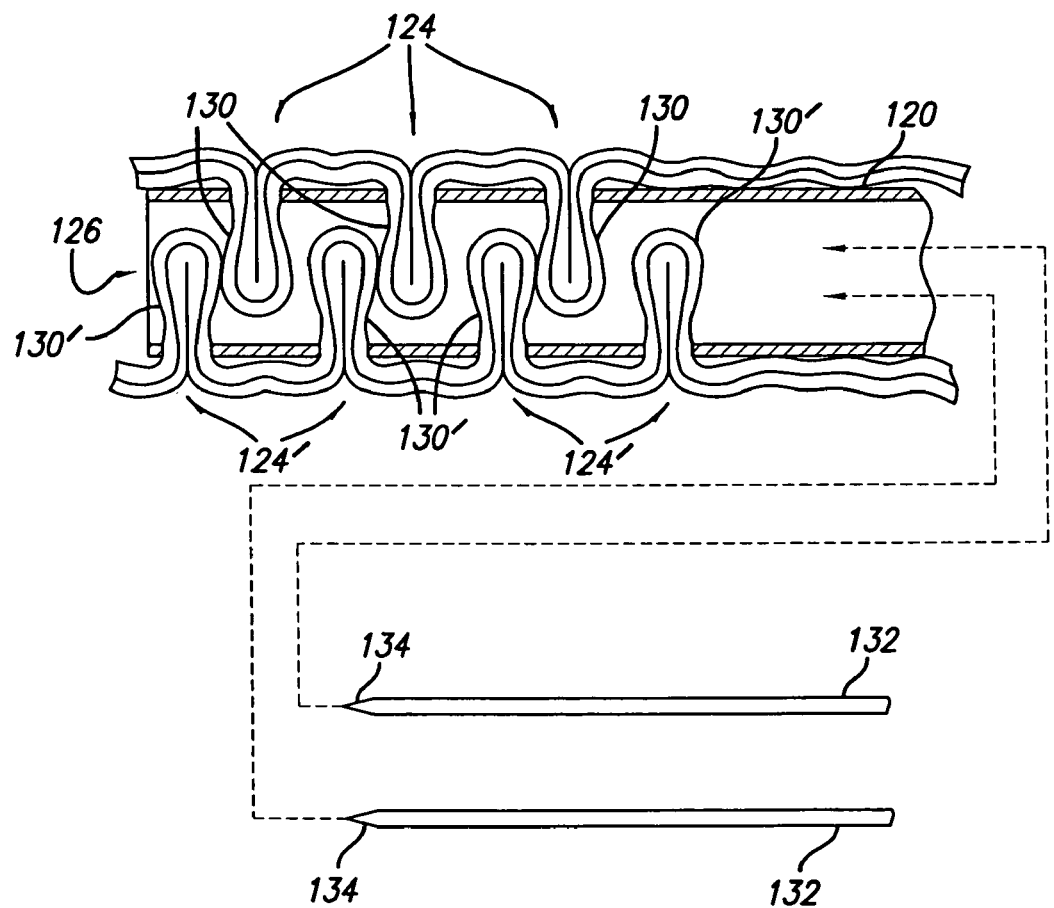
FIG. 12 shows a cross-sectioned side view of the overtube of FIGS. 10A and 10B.

FIG. 12 shows a cross-sectioned side view of overtube 120 from FIGS. 10A to 11B showing the invagination of tissue within. As seen, invaginated tissue 130, 130' may be drawn into lumen 126 through the respective first and second windows 124, 124'. Once drawn within, the overlapping tissue 130, 130' may be fastened to one another using spiral fastener 44 as described above using a drive tube. Alternatively, and as shown, fasteners 132, each preferably having tapered or sharpened distal tips 134, may be driven distally from the proximal end of overtube 120 into each adjacent region of invaginated tissue 130, 130' to fasten them together. Once fastened, overtube 120 may then be withdrawn from the area by simply retracting overtube 120 while maneuvering the fastened tissue through first and second channels 122, 122'. Although two fasteners 132 are shown, any number of fasteners may be utilized depending upon the desired results. Additionally, to aid in preventing the fasteners from backing out of the tissue or from being dislodged, barbs or whisker-like filaments may be formed along its length to protrude and to engage the tissue once the fasteners are in place within the tissue.

The applications of the apparatus and methods of use discussed above are not limited to regions of the body but may include any number of further treatment applications. Other treatment sites may include areas or regions of the body around organ bodies. Additionally, the present invention may be used in other environments which present tortuous paths such as exploratory procedures on piping systems, ducts, etc. Modification of the above-described assemblies and methods for carrying out the invention, and variations of aspects of the invention that are obvious to those of skill in the art are intended to be within the scope of the claims.

We claim:

1. An overtube system for insertion into a body, comprising:
 an elongate overtube having a proximal end, a distal end, and a length therebetween with a first lumen defined through the length, wherein the overtube defines at least one opening near or at the distal end of the overtube and wherein the opening is adapted to adhere tissue thereto; and
 a fastening assembly disposed within the first lumen and adapted to fasten the tissue adhered to the opening.

2. The system of claim 1 wherein the overtube defines at least two openings near or at the distal end of the overtube in apposition with one another.

3. The system of claim 2 wherein the openings are slots longitudinally defined along the length of the overtube.

4. The system of claim 2 wherein the overtube further comprises a wall extending longitudinally within the overtube at least partially and which separates the first lumen between the two openings.

5. The system of claim 1 wherein the overtube defines a plurality of openings near the distal end, wherein each of the openings are defined in an alternating and apposing pattern between adjacent openings.

6. The system of claim 1 wherein the overtube distal end is in fluid communication with the proximal end through the first lumen.

7. The system of claim 1 wherein the fastening assembly comprises an elongated shaft having a proximal end and a distal end with a stapling device attached thereto.

8. The system of claim 1 wherein the fastening assembly comprises a staple.

9. The system of claim 1 wherein the fastening assembly comprises an elongate member having a tapered distal end.

10. The system of claim 1 further comprising a tubular member adjustably disposed within the first lumen, wherein the tubular member defines a second lumen therethrough.

11. The system of claim 10 wherein the tubular member is disposed within the overtube such that the tubular member is rotatable about a longitudinal axis defined by the tubular member.

12. The system of claim 10 wherein the second lumen of the tubular member is adapted to slidingly receive an endoscope shaft.

13. The system of claim 10 wherein the proximal end of the overtube comprises an entry port through which the tubular member is disposed, wherein the entry port is adapted to form a fluid-tight seal with an outer surface of the tubular member.

14. An overtube system for insertion into a body, comprising:

an elongate overtube having a proximal end, a distal end, and a length therebetween with a first lumen defined through the length, wherein the overtube defines at least one opening near or at the distal end of the overtube and wherein the opening is adapted to adhere tissue thereto;

a fastening assembly disposed within the first lumen and adapted to fasten the tissue adhered to the opening; and, a pump in fluid communication with the first lumen of the overtube.

15. The system of claim 14 wherein the pump is connected to the overtube via a fluid port defined near or at the proximal end of the overtube.

16. The system of claim 14 wherein the pump comprises a negative pressure pump.

17. The system of claim 14 wherein the pump comprises a positive pressure pump.

18. An overtube system for insertion into a body, comprising:

an elongate overtube having a proximal end, a distal end, and a length therebetween, wherein the overtube defines at least a first opening and a second opening in apposition with one another near or at the distal end of the overtube, wherein the openings are separated from one another by a wall at least partially extending longitudinally within the overtube such that a first lumen and a second lumen are defined within the overtube, and wherein the openings are adapted to adhere tissue thereto; and a fastening assembly disposed within the overtube and adapted to fasten the tissue adhered to the openings.

* * * * *